United States Patent
Moccand et al.

(10) Patent No.: US 12,167,990 B2
(45) Date of Patent: Dec. 17, 2024

(54) VITAMIN COMPOSITION

(71) Applicant: SOCIÉTÉ DES PRODUITS NESTLÉ S.A., Vevey (CH)

(72) Inventors: Cyril Moccand, Lausanne (CH); Laurent Sagalowicz, Blonay (CH); Nicola Galaffu, Ornex (FR); Martin Michel, Lausanne (CH); Edwin Alberto Habeych Narvaez, Lausanne (CH)

(73) Assignee: Societe des Produits Nestle S.A., Vevey (CH)

( * ) Notice: Subject to any disclaimer, the term of this patent is extended or adjusted under 35 U.S.C. 154(b) by 872 days.

(21) Appl. No.: 16/076,066

(22) PCT Filed: Jan. 25, 2017

(86) PCT No.: PCT/EP2017/051470
§ 371 (c)(1),
(2) Date: Aug. 7, 2018

(87) PCT Pub. No.: WO2017/137255
PCT Pub. Date: Aug. 17, 2017

(65) Prior Publication Data
US 2021/0177774 A1    Jun. 17, 2021

(30) Foreign Application Priority Data
Feb. 11, 2016 (EP) .................... 16155184

(51) Int. Cl.
*A61K 31/07* (2006.01)
*A61K 47/44* (2017.01)
*A61K 47/46* (2006.01)

(52) U.S. Cl.
CPC .............. *A61K 31/07* (2013.01); *A61K 47/44* (2013.01); *A61K 47/46* (2013.01)

(58) Field of Classification Search
CPC .................................................... A61K 31/07
See application file for complete search history.

(56) References Cited

U.S. PATENT DOCUMENTS

| | | | |
|---|---|---|---|
| 2,359,413 A * | 10/1944 | Freedman | A61K 31/16 424/601 |
| 5,550,146 A * | 8/1996 | Acosta | A23L 33/175 514/400 |
| 5,976,575 A | 11/1999 | Gellenbeck | |
| 2006/0257530 A1 | 11/2006 | Hoffpauer | |
| 2007/0128331 A1 | 6/2007 | Kvist et al. | |
| 2012/0064191 A1 | 3/2012 | Lynch et al. | |
| 2013/0071372 A1* | 3/2013 | Naidu | A61K 38/1866 424/94.4 |

FOREIGN PATENT DOCUMENTS

| | | | |
|---|---|---|---|
| CN | 1747658 | A | 3/2006 |
| CN | 101703170 | | 5/2010 |
| CN | 104397409 | A * | 3/2015 |
| CN | 104489411 | | 4/2015 |
| CN | 104782994 | | 7/2015 |
| EP | 2289347 | A1 | 3/2011 |
| GB | 573937 | A | 12/1945 |
| JP | 2007185156 | | 7/2007 |
| JP | 2007244201 | | 9/2007 |

OTHER PUBLICATIONS

Schmidt et al., Bioresource Technology, 123 (2012) 36-41.*
21 CFR 101.62(a)(b), current as of Oct. 24, 2022.*
Robinette et al., Defatted Rice Bran as a Protein Source in Catfish Feeds, Proc. Annu. Confr. Southeast. Assoc. Fish and Wildl. Agencies, 42:51-55, 1988.*
Gupta et al., Reduction of phytic acid and enhancement of bioavailable micronutrients in food grains, J Food Sci Technol (Feb. 2015) 52(2):676-684.*
Database GNPD [Online] MINTEL., "Vanilla Flavoured Meal Replacement Drink", Nov. 10, 2014, pp. 1-3, XP55643950.
European Office Action for Appl No. 17 702 046.8-1106 dated Nov. 25, 2019.
Zhang et al. "Antioxidant activities of the fractionated protein hydrolysates from heat stable defatted rice bran" International Journal of Food Science & Technology, 2014, vol. 49, pp. 1330-1336.
Saunders, R.M. "The Properties of Rice Bran as a Foodstuff" Cereal Foods World, Jul. 1990, vol. 35, No. 7, 4 pages, XP002956826.
Devi et al. "Antioxidant efficacy of phytochemical extracts from defatted rice bran in the bulk oll system" Food Chemistry, 2007, vol. 104, pp. 658-664.
Wu et al. "Development of a database for total antioxidant capacity in foods: a preliminary study" Journal of Food Composition and Analysis, 2004, vol. 17, pp. 407-422.
China Patent Office Communication for Application No. 201780007098. 5, dated Aug. 11, 2021, 19 pages.

* cited by examiner

*Primary Examiner* — Svetlana M Ivanova
(74) *Attorney, Agent, or Firm* — K&L Gates LLP (57) ABSTRACT

A composition comprising: (i) a mixture containing a lipid-soluble vitamin dissolved in a lipid, and (ii) bran; wherein the mixture is absorbed into and/or adsorbed onto the bran and wherein the lipid does not originate from the bran. Also provided are processes for providing a stabilised vitamin composition.

18 Claims, 4 Drawing Sheets

VITAMIN COMPOSITION

CROSS REFERENCE TO RELATED APPLICATIONS

The present application is a National Stage of International Application No. PCT/EP2017/051470, filed on Jan. 25, 2017, which claims priority to European Patent Application No. 16155184.1, filed on Feb. 11, 2016, the entire contents of which are being incorporated herein by reference.

FIELD OF INVENTION

The present invention relates to vitamin compositions and in a particular to vitamin compositions comprising stabilised lipid-soluble vitamins.

BACKGROUND

Lipid-soluble vitamins such as vitamin A and vitamin D are essential for health. By way of example, vitamin A is one of the four micronutrients with the highest deficiencies worldwide, the others being iron, zinc and iodine. It is estimated that 600,000 children under the age of five die each year due to vitamin A deficiency. For this target population, vitamin A is believed to be the micronutrient for which a deficiency causes the highest number of fatalities. Vitamin A deficiency also affects adults, especially pregnant women. First symptoms are night blindness and a decreased efficiency of the immune system. Vitamin A deficiencies occur principally in developing countries due to diets low in vitamin A or provitamin A (a substance converted to vitamin A in the body). Vitamin D deficiency is associated in children with rickets and in adults with osteomalacia.

Food fortification is one method to increase the levels of lipid-soluble vitamin intake, along with dietary diversification. Unfortunately, fortification of foods with lipid-soluble foods such as vitamin A or provitamin A can be difficult. Vitamin A for example is sensitive to heat, light and oxidation, with large losses of vitamin A activity occurring during processing, transportation and storage of fortified foods. Lipid soluble vitamins such as vitamin A may further be destroyed if the fortified foods are cooked, for example by boiling. Adding vitamins at levels above the intended fortification level to compensate for losses is costly and also undesirable because of the potential for overdosing. This problem is especially acute for lipid soluble vitamins which accumulate in the body. For example vitamin A accumulates in adipose tissue and high levels are acutely toxic.

Food products providing lipid-soluble vitamins in developing countries must be affordable in order to be obtainable by those in need. It would therefore be desirable to provide a stabilised form of a lipid-soluble vitamin such as vitamin A, vitamin A esters, provitamin A, vitamin D and vitamin D esters, especially one which can be safely be consumed.

Vitamin A may be stabilized in compositions by including high levels of synthetic antioxidants, but this is not always desirable to consumers who seek products with familiar ingredients of natural origin. Vitamin A may be encapsulated, for example by spray drying an emulsion of vitamin A in a glassy matrix made of modified and non-modified starch. However this approach to stabilization is complex and adds considerable processing cost to the material.

SUMMARY OF INVENTION

The present invention addresses the above prior art problems by providing a vitamin composition, together with processes for providing a vitamin composition, as described in the claims.

In one aspect, the invention provides a composition comprising (i) a mixture containing a lipid-soluble vitamin dissolved in a lipid, and (ii) bran; wherein the mixture is absorbed into and/or adsorbed onto the bran and wherein the lipid does not originate from the bran.

In one embodiment, the lipid-soluble vitamin is selected from the group consisting of: vitamin A, provitamin A, vitamin D, vitamin A ester, vitamin D ester, and combinations thereof.

In one embodiment, the lipid-soluble vitamin is selected from the group consisting of vitamin A, provitamin A and vitamin A ester, and combinations thereof.

In one embodiment, the ester is selected from an acetate or a fatty acid ester, and a combination thereof.

In one embodiment, the lipid-soluble vitamin is selected from the group consisting of: vitamin A fatty acid ester and provitamin A, and a combination thereof.

In one embodiment, the lipid-soluble vitamin is vitamin A fatty acid ester, preferably selected from the group consisting of retinyl palmitate, retinyl oleate, retinyl stearate and retinyl linoleate, and combinations thereof, preferably wherein the lipid-soluble vitamin is retinyl palmitate. Retinyl palmitate is another name for vitamin A palmitate.

In one embodiment, the provitamin A is beta-carotene or beta-cryptoxanthin.

In one embodiment, the lipid-soluble vitamin is selected from the group consisting of vitamin D and a vitamin D ester, and combinations thereof.

In one embodiment, the lipid-soluble vitamin is selected from the group consisting of: cholecalciferol (vitamin D3) and ergocalciferol (vitamin D2), an ester of cholecalciferol and an ester of ergocalciferol.

In one embodiment, the ester is selected from the group consisting of acetate, palmitate, oleate, stearate and linoleate, preferably palmitate.

In one embodiment, the lipid is a fat. The fat may be fish oil, animal fat or vegetable fat. For example, the animal fat may be extracted from the rendered tissue of livestock animals like pigs, chickens and cows, or may be dairy fats such as butter fat. The vegetable fat may be selected from the group consisting of sunflower oil, rapeseed oil, cottonseed oil, coconut oil, cocoa butter, illipe fat, sal fat, shea fat, olive oil, palm oil, soybean oil, peanut oil, palm kernel oil, corn oil, grape seed oil, hazelnut oil, sesame oil and mixtures of these. The fat may be liquid at 25° C. Preferably the fat is selected from palm oil and sunflower oil; more preferably the lipid is palm oil.

In one embodiment, the bran is powdered bran.

In one embodiment, the bran is defatted bran.

In one embodiment, the bran has a reduced phytic acid content; preferably wherein the bran has less than about 5 wt. % phytic acid, preferably less than about 2.5 wt % phytic acid, more preferably less than about 1.5 wt % phytic acid.

The bran comprised within the composition of the invention may be derived from the major cereals consumed worldwide: wheat, buckwheat, rice, maize, barley, oats, rye, millet, and sorghum. In one embodiment, the bran is selected from rice bran, wheat bran, oat bran, and combinations thereof; preferably wherein the bran is rice bran.

The bran comprised within the composition of the invention may be oat bran. Consumption of oat bran has been shown to lower low-density lipoprotein (LDL) and total cholesterol [A. Whitehead et al., Am J Clin Nutr 100 (6): 1413-21 (2014)] which may reduce the risk of heart disease.

In one embodiment, the weight ratio of (i) to (ii) is from: about 1:200 to about 1:1, about 1:100 to about 1:1.5, about 1:50 to about 1:2, about 1:20 to about 1:2, about 1:10 to about 1:2, or about 1:6 to about 1:3.

In one embodiment, the amount of lipid-soluble vitamin in the lipid is from about 0.1 to about 5 wt. %; preferably from about 0.1 wt. % to about 4 wt. %, about 0.1 wt. % to about 3 wt. %, about 0.1 wt. % to about 2 wt. %, or about 0.1 wt. % to about 1 wt. %.

In one embodiment, the bran comprises about 0.001 wt. % to about 2.5 wt. % lipid-soluble vitamin; preferably about 0.05 wt. % to about 1 wt. %, about 0.01 wt. % to about 0.5, about 0.05 wt. % to about 0.5 wt. %, about 0.1 wt. % to about 0.25 wt. %, or about 0.1 to about 0.2 wt. % lipid-soluble vitamin.

In one embodiment, the composition further comprises an antioxidant.

In one embodiment, the composition further comprises an emulsifier; preferably wherein the emulsifier is lecithin.

In one embodiment, the ratio of the amount of lipid-soluble vitamin present in the composition following a storage period of about 20 days at about 60° C. and about 68% relative humidity to the amount of lipid-soluble vitamin present in the composition at the start of the same storage period is at least 0.5:1; preferably at least 0.6:1, more preferably at least 0.7:1.

In one embodiment, the ratio of the amount of lipid-soluble vitamin present in the composition following exposure for about one hour to a temperature of about 98° C. to the amount of lipid-soluble vitamin present in the composition before said exposure is at least 0.8:1, preferably at least 0.9:1.

In another aspect, the invention provides a process for preparing a composition as described above comprising the steps of: (a) dissolving a lipid-soluble vitamin in a lipid to form a mixture; and (b) combining the mixture with bran, thereby absorbing the mixture into and/or adsorbing the mixture onto the bran.

In another aspect, the invention provides a process for providing a stabilised vitamin composition, the process comprising the steps of: (a) dissolving a lipid-soluble vitamin in a lipid to form a mixture; and (b) combining the mixture with bran, absorbing the mixture into and/or adsorbing the mixture onto the bran to provide a stabilized vitamin composition.

In one embodiment, the lipid-soluble vitamin is as defined above with regard to the composition of the invention.

In one embodiment, the lipid as defined above with regard to the composition of the invention.

In one embodiment, the bran is as defined above with regard to the composition of the invention.

In one embodiment, the weight ratio of lipid to bran is from: about 1:200 to about 1:2, about 1:100 to about 1:2, about 1:50 to about 1:2, about 1:20 to about 1:2, about 1:10 to about 1:2, or about 1:6 to about 1:3.

In one embodiment, the amount of lipid-soluble vitamin in the lipid is from about 0.1 to about 5 wt. %; preferably from about 0.1 wt. % to about 4 wt. %, about 0.1 wt. % to about 3 wt. %, about 0.1 wt. % to about 2 wt. %, or about 0.1 wt. % to about 1 wt. %.

In one embodiment, the bran comprises about 0.001 wt. % to about 2.5 wt. % lipid-soluble vitamin; preferably about 0.05 wt. % to about 1 wt. %, about 0.01 wt. % to about 0.5, about 0.05 wt. % to about 0.5 wt. %, about 0.1 wt. % to about 0.25 wt. %, or about 0.1 to about 0.2 wt. % lipid-soluble vitamin.

In one embodiment, the weight ratio of the mixture containing lipid-soluble vitamin and lipid to bran is from: about 1:200 to about 1:1, about 1:100 to about 1:1.5, about 1:50 to about 1:2, about 1:20 to about 1:2, about 1:10 to about 1:2, or about 1:6 to about 1:3.

In another aspect, the invention provides a composition obtainable by a process as described above.

In another aspect, the invention provides a food product comprising a composition as defined above.

In one embodiment, the food product is selected from the group consisting of: a dairy product, a culinary product, a food ingredient, a baked good, a beverage product, a beverage powder, a confectionary product, a pasta or noodle product, a milk powder, a soup, a sauce, a taste maker and a pet food.

In another aspect, the invention provides a nutritional supplement comprising the composition as defined above.

In one embodiment, the nutritional supplement is a maternal supplement.

In another aspect, the invention provides the use of bran for stabilising a lipid-soluble vitamin, wherein the lipid-soluble vitamin is dissolved in a lipid and wherein the lipid is absorbed into the bran.

In one embodiment, the lipid-soluble vitamin is as defined above.

In one embodiment, the lipid as defined above.

In one embodiment, the bran is as defined above.

DETAILED DESCRIPTION OF INVENTION

The present invention provides a composition comprising (i) a mixture containing a lipid-soluble vitamin dissolved in a lipid, and (ii) bran; wherein the mixture is absorbed into and/or adsorbed onto the bran and wherein the lipid does not originate from the bran. In an embodiment of the composition of the invention, neither the lipid nor the lipid-soluble vitamin originate from the bran.

The inventors have found that the stability of a lipid-soluble vitamin can be increased by dissolving the lipid-soluble vitamin in a lipid carrier such as an oil to form a mixture, and absorbing the mixture into bran. The stabilised vitamin has increased resistance to degradation by heat and during storage.

The inventors were surprised to find this increase in stability, as the antioxidant capacity of rice bran with vitamin A (as measured by oxygen radical absorbance capacity) decreases in the presence of lipid (see Example 1). The increased stability is therefore not primarily an antioxidant effect. Without wishing to be bound by theory, the inventors believe that the high oil-binding capacity of bran, together with endogenous antioxidants and specific structures containing waxes, stabilise the vitamin by the formation of organogels, enabling natural encapsulation and stabilisation of the vitamin.

The resultant composition provides a lipid-soluble vitamin that is significantly stabilised against degradation, such as degradation caused by heat, light or storage. The composition may be added to a food product in order to fortify the food product with the lipid-soluble vitamin. Advantageously, the increased stability of the lipid-soluble vitamin means that it is not necessary to over-fortify the food product to compensate for vitamin degradation, thus avoiding potential problems of vitamin overdosing such as can occur for example with excessive consumption of vitamin A.

In addition, stabilisation of a lipid-soluble vitamin with bran according to the invention also avoids the need to use artificial or synthetic vitamin-stabilising compounds. This provides an additional advantage as the use of artificial or synthetic compounds in food products can be negatively perceived by consumers.

Lipid which does not originate from the bran is lipid which was not initially present in the bran, for example lipid which was not part of the natural lipids of the bran.

In one embodiment, the mixture is absorbed into the bran. In another embodiment, the mixture is adsorbed onto the bran. In a further embodiment, the mixture is absorbed into and adsorbed onto the bran.

Lipid-soluble vitamins are a group that include vitamins A, D, E and K. Vitamins A and D are particularly suitable for use in the present invention. In a particularly preferred embodiment, the lipid-soluble vitamin in the composition of the invention is vitamin A or provitamin A.

Vitamin A is the name of a group of fat-soluble retinoids, including retinol, retinal, retinoic acid, and retinyl esters. Vitamin A is involved in immune function, vision, reproduction, and cellular communication. Vitamin A also supports cell growth and differentiation, playing a critical role in the normal formation and maintenance of the heart, lungs, kidneys, and other organs. Two forms of vitamin A are available in the human diet: preformed vitamin A (retinol and its esterified form, retinyl ester) and provitamin A. Preformed vitamin A is found in foods from animal sources, including dairy products, fish, and meat (especially liver). By far the most important provitamin A is beta-carotene; other types of provitamin A are alpha-carotene and beta-cryptoxanthin. The body converts these plant pigments into vitamin A. Both provitamin A and preformed vitamin A must be metabolised intracellularly to retinal and retinoic acid, the active forms of vitamin A, to support the vitamin's important functions.

Vitamin A in the composition of the invention may be vitamin A or a vitamin A ester. In one embodiment, the vitamin A ester is vitamin A acetate or a vitamin A fatty acid ester (retinyl ester). In one embodiment, the vitamin A fatty acid ester is selected from the group consisting of retinyl palmitate, retinyl oleate, retinyl stearate and retinyl linoleate, and combinations thereof. Preferably, the vitamin A is vitamin A palmitate (retinyl palmitate).

Vitamin D is obtained from food and can also be produced endogenously by the action of ultraviolet light from sunlight on skin. Vitamin D obtained from food and via sun exposure is biologically inert and must undergo two hydroxylation reactions in the live and kidneys to provide activity. Vitamin D is converted in the liver to 25-hydroxyvitamin D, also known as calcidiol. The physiologically active 1,25-dihydroxyvitamin D (also known as calcitriol) is formed in the kidneys. Vitamin D promotes calcium absorption in the gut and maintains serum calcium and phosphate concentrations to enable normal bone mineralisation and prevent hypocalcemic tetany. Vitamin D is also required for bone growth and bone remodelling by osteoblasts and osteoclasts. In the absence of sufficient amounts of vitamin D, bones can become thin, brittle or misshapen. Vitamin D insufficiency leads to rickets in children and osteomalacia in adults. Vitamin D together with calcium can also protect against osteoporosis in older adults. Additional roles of vitamin D in the body include the modulation of cell growth, neuromuscular and immune function, and the reduction of inflammation.

Vitamin D in the composition of the invention may be vitamin D or a vitamin D ester. The vitamin D may be selected from cholecalciferol (vitamin D3), ergocalciferol (vitamin D2), calcidiol and calcitriol, and esters thereof. The vitamin D may be selected from cholecalciferol, ergocalciferol, and esters thereof. Vitamin D esters may be selected from group consisting of acetate, palmitate, oleate, stearate and linoleate esters. In one embodiment, the vitamin D ester is vitamin D palmitate.

The composition of the present invention comprises a lipid, in which the lipid-soluble vitamin is dissolved. The lipid therefore functions as a carrier solvent, enabling the dissolved vitamin to be absorbed into and/or adsorbed onto the bran.

Lipids suitable for use in the present invention are lipids suitable for consumption by humans and/or animals. In a preferred embodiment, the lipid is a vegetable oil. Vegetable oils are edible triglyceride oils derived from plants. The lipid of the composition of the invention may comprise medium chain triglycerides, for example the lipid may consist of medium chain triglycerides. Medium-chain triglycerides (MCTs) are triglycerides whose fatty acids have an aliphatic tail of 6-12 carbon atoms.

In one embodiment, the lipid is sunflower oil or palm oil.

Sunflower oil is produced from seeds of the sunflower plant. Sunflower oil is primarily composed of triglycerides derived from the fatty acids linoleic acid and oleic acid. Sunflower oil is commonly used in cooking as a frying oil.

Palm oil is derived from the fruit of oil palms, a genus of palm trees. Palm oil triglycerides are primarily derived from the fatty acids myristic acid, palmitic acid, stearic acid, oleic acid, and linoleic acid.

In one embodiment, the lipid is palm oil. The present inventors have found that use of palm oil in the compositions of the present invention, especially in combination with vitamin A, provides particularly advantageous results.

Bran is formed from the outer layers of cereal grains. Brans, also known as cereal brans, are milling fractions containing pericarp, testa, aleurone layer, germ, and part of the starchy endosperm. Brans can be derived from the major cereals consumed worldwide: wheat, rice, maize, barley, oats, rye, millet, and sorghum. Depending on the type of cereal grain, the bran constitutes approximately 3-30% of the kernel dry weight. Brans are rich in dietary fibre, minerals, vitamin B, and bioactive compounds. A key component of the bran, the aleurone layer, is relatively high in ash, protein, total phosphorus, phytate phosphorus, fat and niacin. Brans can be used to impart texture, gelling, thickening and emulsifying properties to foods.

The makeup of brans from different cereals is shown in Table 1 below:

defatted bran may be produced by removing all or part of the oil fraction using a technique such as solvent extraction or pressing.

Defatted bran may contain less than about 5 wt. % fat, less than about 4 wt. % fat, less than about 3 wt. % fat, less than about 2 wt. % fat, less than about 1.5 wt. % fat, less than about 1 wt. % fat, or less than about 0.5 wt. % fat.

In a preferred embodiment, the bran is rice bran. The inventors have found that particularly advantageous results are produced when the bran is rice bran. Preferably, in any aspect or embodiment of the present invention as defined herein, the rice bran is defatted rice bran.

In one embodiment, the bran has been treated to remove or reduce the concentration of phytic acid. Thus, in one embodiment, the bran has a reduced phytic acid content. Phytic acid may be extracted from bran by solid/liquid extraction conducted at 25° C. for 30 minutes using hydrochloric acid at pH 2 as solvent.

Phytic acid (inositolhexakisphosphate) is a plant storage form of phosphorus that is found in plant tissues including bran. Phytic acid consumption in animals can interfere with the absorption of the B vitamin niacin; phytic acid can therefore function as an anti-nutrient. In one embodiment, the bran has less than about 5 wt. %, less than about 4 wt. %, less than about 3 wt. %, less than about 2 wt. %, less than about 1 wt. %, less than about 0.5 wt. %, or less than about 0.25 wt. % phytic acid.

In one embodiment, the weight ratio of (i) to (ii) [i.e. the weight ratio of component (i) of the composition to component (ii)] is from: about 1:200 to about 1:1, about 1:100 to about 1:1.5, about 1:50 to about 1:2, about 1:20 to about

TABLE 1

| Parameter | Rice | Wheat | Corn | Oats | Barley | Rye | Sorghum | Millet |
| --- | --- | --- | --- | --- | --- | --- | --- | --- |
| Protein (%) | 11.8-15.6 | 9.6-17.1 | 6.6-11.5 | 8.8-16.7 | 11.2-14.0 | 14.6 | 7.7-15.0 | 11.5 |
| Ash (%) | 6.6-10.0 | 4.0-6.5 | 0.9-3.4 | 1.5-6.3 | 3.1-5.0 | 4.2 | 2.1-3.0 | 10.5 |
| Fat (%) | 6.0-19.7 | 2.9-4.8 | 1.1-8.1 | 3.0-10.6 | 2.8-5.0 | 2.6 | 4.6-4.7 | 8.0 |
| Total fibre (%) | 27.0 | 48.0 | 88.1 | 24.7 | 72.5 | 35.8 | [unknown] | [unknown] |
| Soluble dietary fibre (%) | 2.5 | 2.4 | 2.1 | 11.7 | 3.1 | 5.3 | [unknown] | [unknown] |
| Insoluble dietary fibre (%) | 24.5 | 45.6 | 86.0 | 13.0 | 69.4 | 30.5 | [unknown] | [unknown] |
| Carbohydrate (%) | 31.1-52.3 | 50.7-59.2 | 58.9-62.6 | 55.6-61.4 | 51.9-58.4 | 58.0 | 54.3-64.1 | 56.0 |

The bran in the composition of the invention may be powdered or coarse. In a preferred embodiment, the bran is powdered bran. Methods of producing powdered bran are known in the art.

The powdered bran may have a particle size of from about 15 μm to about 1000 μm, for example about 50 μm to about 800 μm, about 75 μm to about 700 μm, about 100 μm to about 600 μm, or about 250 μm to about 500 μm. Particle size and particle size distribution may be measured by laser diffraction using a Malvern Mastersizer (e.g using the Fraunhofer approximation).

In one embodiment, the bran is defatted bran. The inventors have found that particularly advantageous results are produced when the bran is defatted bran. Defatted bran is produced by removal of the fat component from bran. Notably, the fat component is believed to contain the majority of bran antioxidant activity. Methods for producing defatted bran are known in the art. By way of example, 1:2, about 1:10 to about 1:2, or about 1:6 to about 1:3; preferably about 1:10 to about 1:2; more preferably about 1:6 to about 1:3.

In one embodiment, the amount of lipid-soluble vitamin in the lipid is from about 0.1 to about 5 wt. %; for example, about 0.1 wt. % to about 4 wt. %, about 0.1 wt. % to about 3 wt. %, about 0.1 wt. % to about 2 wt. %, or about 0.1 wt. % to about 1 wt. %.

In one embodiment, the amount of lipid-soluble vitamin in the lipid is from about 0.1 wt. % to about 2 wt. %; for example, about 0.2 wt. % to about 1.8 wt. %, about 0.2 to about 1.6 wt. %, about 0.4 wt. % to about 1.6 wt. %, or about 0.5 wt. % to about 1.5 wt. %.

In one embodiment, the amount of lipid-soluble vitamin in the lipid is about 0.1, 0.2, 0.3, 0.4, 0.5, 0.6, 0.7, 0.8, 0.9, 1.0, 1.1, 1.2, 1.3, 1.4, 1.5, 2.0, 2.5, 3.0, 3.5, 4.0, 4.5 or 5.0 wt. %.

In one embodiment, the bran comprises about 0.0005 wt. % to about 2.5 wt. % lipid-soluble vitamin; for example about 0.05 wt. % to about 1 wt. %, about 0.01 wt. % to about 0.5, about 0.05 wt. % to about 0.5 wt. %, about 0.1 wt. % to about 0.25 wt. %, or about 0.1 to about 0.2 wt. % lipid-soluble vitamin; preferably about 0.1 wt. % to about 0.25 wt. %, or about 0.1 to about 0.2 wt. % lipid-soluble vitamin. The bran may comprise less than 0.004% lipid-soluble vitamin.

The composition of the invention may further comprise an antioxidant. Preferably the antioxidant is present in component (i) of the composition.

The presence of an antioxidant may further enhance the stability of the lipid-soluble vitamin.

As used herein, the term "antioxidant" is understood to include any one or more of various substances that inhibit oxidation or reactions promoted by Reactive Oxygen Species (ROS) and other radical or non-radical species. Additionally, antioxidants are molecules capable of slowing or preventing the oxidation of other molecules. Non-limiting examples of antioxidants include coenzyme Q10 (coQ10), flavonoids, glutathione, Goji (wolfberry), hesperidine, lactowolfberry, lignin, lutein, lycopene, polyphenols, selenium, vitamin B1, vitamin B6, vitamin B12, vitamin C, vitamin D, vitamin E, zeazanthin, synthetic antioxidants, citric acid or combinations thereof. The antioxidant may be selected from the group consisting of ascorbyl palmitate, rosemary extract, citric acid, green tea extract, tocopherol, butylated hydroxytoluene (BHT), butylated hydroxyanisole (BHA), tert-butylhydroquinone (TBHQ) and combinations of these. The antioxidant may be selected from the group consisting of ascorbyl palmitate, rosemary extract, citric acid, green tea extract, butylated hydroxytoluene (BHT), butylated hydroxyanisole (BHA), tert-butylhydroquinone (TBHQ) and combinations of these. The antioxidant may be a butylated phenol, for example butylated hydroxytoluene (BHT), butylated hydroxyanisolate (BHA), tert-butylhydroquinone (TBHQ). The antioxidant may be butylated hydroxytoluene. The antioxidant may be tocopherol. The antioxidant may comprise a mixture of butylated hydroxytoluene (BHT) and butylated hydroxyanisole (BHA), for example the antioxidant may comprise a mixture of butylated hydroxytoluene (BHT) and butylated hydroxyanisole (BHA) and the lipid-soluble vitamin may comprise vitamin A palmitate.

The antioxidant may be present at a concentration of: about 0.005 wt. % to about 0.5 wt. %, about 0.01 wt. % to about 0.5 wt. %, about 0.01 wt. % to about 0.4 wt. %, about 0.01 wt. % to about 0.2 wt. %, about 0.02 wt. % to about 0.4 wt. %, or about 0.02 wt. % to about 0.2 wt. % relative to the lipid in component (i). The antioxidant may be present at a concentration of about: 0.005, 0.01, 0.02, 0.03, 0.04, 0.05, 0.1, 0.2, 0.3, 0.4, or 0.5 wt. % relative to the lipid in component (i).

The composition of the invention may further comprise an emulsifier. Preferably the emulsifier is present in component (i) of the composition.

An example of a suitable emulsifier is lecithin. The term lecithin refers to a group of fatty substances found in animal and plant tissues, which are composed of phospholipids and have amphiphilic properties making them suitable for use as emulsifiers. In one embodiment, the composition of the invention comprises lecithin.

The emulsifier may be present at a concentration of: about 0.1 wt. % to about 30 wt, about 0.5 wt. % to about 30 wt. %, about 0.5 wt. % to about 20 wt. %, about 1 wt. % to about 20 wt. %, about 1 wt. % to about 10 wt. %, or about 2 wt. % to about 5 wt. % relative to the lipid in component (i). The emulsifier may be present at a concentration of about: 0.1, 0.5, 1, 2, 5, 10, or 30 wt. % relative to the lipid in component (i).

The composition of the invention may further comprise one or more additional minerals. In one embodiment, the composition further comprises iron and/or zinc.

Each additional mineral may be present in the composition at a concentration of about 0.1 mg to about 10 mg per gram of bran; for example about 0.5 mg to about 10 mg per gram of bran, about 0.5 mg to about 5 mg per gram of bran, about 1 mg to about 5 mg per gram of bran, or about 1 mg to about 2 mg per gram of bran. Each additional mineral may be present in the composition at a concentration of about 0.1, 0.2, 0.3, 0.4, 0.5, 1, 2, 3, 4, 5 or 10 mg per gram of bran.

The composition of the invention may further comprise water. It is beneficial that the composition of the invention provides good lipid-soluble vitamin stability in systems with appreciable levels of moisture such as are commonly found in food products. The composition may further comprise water and have a water activity greater than about 0.3, for example greater than about 0.4, for further example greater than about 0.45, for further example greater than about 0.50. The composition may have a water activity between about 0.3 and about 0.99, for example between about 0.4 and about 0.95.

In the context of the present invention, the term water activity is defined in the manner common in food science:

$$A_w = P/P_0$$

where $A_w$ is the water activity, P is the vapour pressure of water in the food, and $P_0$ is the vapour pressure of pure water at the same temperature [Wiley Encyclopedia of Food Science and Technology, $2^{nd}$ Edition, 2614 (2000)].

The composition of the invention, as described above, provides improved vitamin stability properties. Thus, in one embodiment, the ratio of the amount of lipid-soluble vitamin present in the composition following a storage period of about 20 days at about 60° C. and about 68% relative humidity to the amount of lipid-soluble vitamin present in the composition at the start of the same storage period is at least 0.5:1; preferably at least 0.6:1, more preferably at least 0.7:1.

In one embodiment, the ratio of the amount of lipid-soluble vitamin present in the composition following exposure for about one hour to a temperature of about 98° C. to the amount of lipid-soluble vitamin present in the composition before said exposure is at least 0.8:1, preferably at least 0.9:1.

The composition of the invention may advantageously be added to a food product in order to fortify it with the lipid-soluble vitamin present in the composition. This thereby provides a stabilised lipid-soluble vitamin to be consumed orally. Examples of food products which may be fortified using a lipid-soluble vitamin provided in the composition of the invention include a dairy product, a culinary product, a food ingredient, a baked good, a beverage product, a beverage powder, a confectionery product, a pasta or noodle product, a milk powder, a soup, a sauce, a taste maker and a pet food. Taste makers and sauces provide a good vehicle for food fortification in a target population as they are relatively inexpensive and may be used in many different target meals. The composition of the invention may be added to a seasoning or bouillon tablet.

The composition of the invention may also advantageously be added to a nutritional supplement in order to fortify it with the lipid-soluble vitamin present in the composition. An example of a suitable nutritional supplement to which the composition of the invention may be added is a maternal supplement.

The present invention also provides a process for providing a composition as described above, the process comprising the steps of (a) dissolving a lipid-soluble vitamin in a lipid to form a mixture; and (b) combining the mixture with bran, thereby absorbing the mixture into and/or adsorbing the mixture onto the bran.

The present invention also provides a process for providing a stabilised vitamin composition, the process comprising the steps of: (a) dissolving a lipid-soluble vitamin in a lipid to form a mixture; and (b) combining the mixture with bran, absorbing the mixture into and/or adsorbing the mixture onto the bran to provide a stabilized vitamin composition.

The lipid-soluble vitamin for use in a process of the invention is a lipid-soluble vitamin as described above with regard to the composition of the invention.

The lipid for use in the process of the invention is a lipid as described above with regard to the composition of the invention.

The bran for use in the process of the invention is a bran as described above with regard to the composition of the invention.

In one embodiment, the weight ratio of lipid to bran is from: about 1:200 to about 1:1, about 1:100 to about 1:1.5, about 1:50 to about 1:2, about 1:20 to about 1:2, about 1:10 to about 1:2, or about 1:6 to about 1:3.

In one embodiment, the amount of lipid-soluble vitamin in the lipid is from about 0.1 to about 5 wt. %; preferably from about 0.1 wt. % to about 4 wt. %, about 0.1 wt. % to about 3 wt. %, about 0.1 wt. % to about 2 wt. %, or about 0.1 wt. % to about 1 wt. %.

In one embodiment, the bran comprises about 0.001 wt. % to about 1 wt. % lipid-soluble vitamin; preferably about 0.05 wt. % to about 1 wt. %, about 0.01 wt. % to about 0.5, about 0.05 wt. % to about 0.5 wt. %, about 0.1 wt. % to about 0.25 wt. %, or about 0.1 to about 0.2 wt. % lipid-soluble vitamin.

In one embodiment, the weight ratio of the mixture containing lipid-soluble vitamin and lipid to bran is from: about 1:200 to about 1:1, about 1:100 to about 1:1.5, about 1:50 to about 1:2, about 1:20 to about 1:2, about 1:10 to about 1:2, or about 1:6 to about 1:3.

Those skilled in the art will understand that they can freely combine all features of the present invention disclosed herein. In particular, features described for the product of the present invention may be combined with the process of the present invention and vice versa.

Furthermore, features described for different embodiments of the present invention may be combined. Where known equivalents exist to specific features, such equivalents are incorporated as if specifically referred to in this specification. Further advantages and features of the present invention are apparent from the Figures and non-limiting Examples.

EXAMPLES

Example 1—Degradation of Vitamin a in Bran Containing Oil Compared to Other Stabilising Solutions Palm oil (SUNIA), and vitamin A palmitate (Vitamin A Palmitate 1.7 MIU/g-DSM) were heated in an oven at 60°. Vitamin A palmitate was not held above 60° C. for longer than 5 minutes to avoid possible degradation. The oil was mixed with vitamin A palmitate in a 0.5 liter Schott bottle and then stirred for 10 minutes in a 50° C. water bath. Initial vitamin A palmitate content was 0.825% in oil (a vitamin A palmitate content of 0.165 wt. % in powdered bran). The total amount of lipid was 100 g. A quantity of 10 g of lipid containing vitamin A palmitate was then mixed with 40 g of powdered rice bran with or without phytic acid (Herba Ingredients) in a mortar during 5 minutes. 10 g of the mixture was transferred to a brown plastic bottle and directly frozen before any heat treatment. This sample was used to determine the initial value of vitamin A ($T_0$). All initial values obtained were in the expected range (5% uncertainty). The remaining sample was transferred in a crystallizing dish and used for storage tests.

In parallel, the lipid mixture containing 0.825% of vitamin A palmitate in oil was aliquoted in 5 samples of 5 g each. One sample was transferred to a brown plastic bottle and frozen before any heat treatment, as above ($T_0$). The 4 remaining samples were transferred in crystallizing dishes and used for storage tests.

Vitamin A palmitate alone was also aliquoted in 5 samples of 5 g each. One sample was transferred to a brown plastic bottle and frozen before any heat treatment, as above ($T_0$). The 4 remaining samples were transferred in crystallizing dishes and used for storage tests.

A quantity of 10 g of lipid containing 0.825 wt. % of vitamin A palmitate was mixed with 40 g of wheat bran in a mortar during 5 minutes. 10 g of the mixture was transferred to a brown plastic bottle and directly frozen before any heat treatment, as above ($T_0$). The remaining sample was transferred in a crystallizing dish and used for storage tests.

A quantity of 10 g of lipid containing 0.825 wt. % of vitamin A palmitate was mixed with 40 g of maltodextrin DE21 in a mortar during 5 minutes. 10 g of the mixture was transferred to a brown plastic bottle and directly frozen before any heat treatment, as above ($T_0$). The remaining sample was transferred in a crystallizing dish and used for storage tests.

A quantity of 10 g of lipid containing 0.825 wt. % of vitamin A palmitate and 1.87 g of iron pyrophosphate powder were mixed with 38.13 g of powdered rice bran (Herba Ingredients) in a mortar during 5 minutes. 10 g of the mixture was transferred to a brown plastic bottle and directly frozen before any heat treatment, as above ($T_0$). The remaining sample was transferred in a crystallizing dish and used for storage tests.

Hexane (29.75 g) was mixed with 0.248 g. vitamin A palmitate for 5 minutes at room temperature with a stirrer. A quantity of 10 g of hexane containing 0.825 wt. % of vitamin A palmitate was mixed with 40 g of powdered rice bran (Herba Ingredients) in a mortar for 5 minutes. The whole sample was subjected to vacuum at 37° C. for 1 hour in a BUCHI Rotavapor® in order to evaporate hexane. 8 g of the mixture was then transferred to a brown plastic bottle and directly frozen before any heat treatment, as above ($T_0$). The remaining sample was transferred in a crystallizing dish and used for storage tests.

For the storage tests, the crystallizing dishes were transferred into a climatic chamber regulated at 60° C. and 68% relative humidity, before being analyzed. Vitamin A analysis was performed by UPLC. Before proceeding with chromatography, the solution containing vitamin A was subjected to a hot saponification step for 30 minutes at 85° C. in ethanol with 7 g potassium hydroxide, followed by solid phase extraction using 100 mL n-hexane for elution. Solvent was evaporated using a rotary evaporator and extract dissolved in 5 mL n-hexane was injected to the UPLC for vitamin A analysis. Chromatography was performed with an Acquity UPLC BEH HILIC 1.7 µm 2.1×100 mm analytical column in normal phase at 1.2 mL/min, using 1% 2-propanol in n-hexane as mobile phase. Vitamin A was detected by UV at 326 nm and expressed in µg of Retinol Equivalent (RE) per 100 g.

Figure 1:
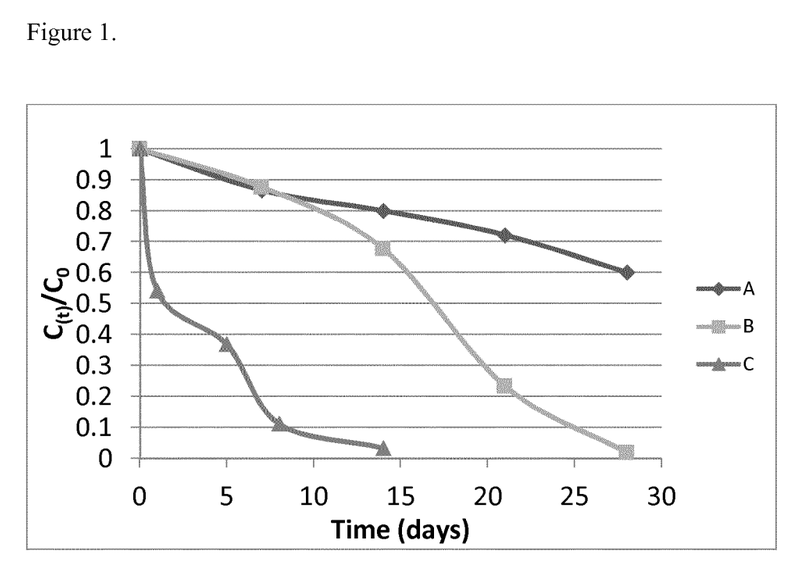
FIG. 1 shows vitamin A degradation curves at 60° C. and 68% RH for bran (rice) containing 20 wt. % of palm oil which contains 0.825 wt. % vitamin A palmitate (A), palm oil containing 0.825 wt. % vitamin A palmitate (B) and vitamin A palmitate alone (C).

The degradation curves are shown in FIGS. 1 to 6. In FIG. 1, we observed that vitamin A palmitate alone is very sensitive to temperature and degrades fast. Adding triglycerides (palm oil) to vitamin A enables a first level of stabilization. Surprisingly, mixing bran with palm oil and vitamin A palmitate increases even more the stability of the vitamin.

Figure 2:
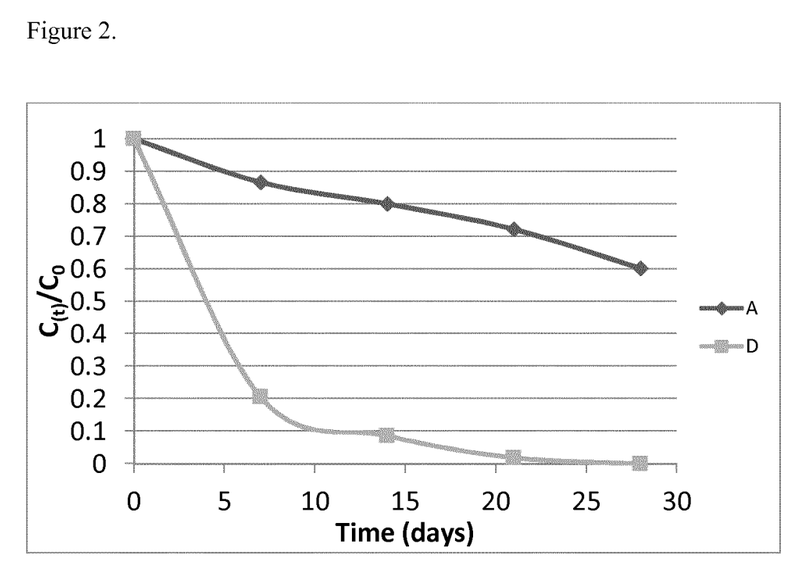
FIG. 2 shows vitamin A degradation curves at 60° C. and 68% RH for bran (rice) containing 20 wt. % of palm oil which contains 0.825 wt. % vitamin A palmitate (A), maltodextrin containing 20 wt. % of palm oil which contains 0.825 wt. % vitamin A palmitate (D).

FIG. 2 displays the degradation curves of palm oil and vitamin A palmitate, either mixed with bran or with maltodextrin, a usual encapsulation carrier for sensitive materials used in the food industry. We showed that bran substantially increases vitamin A stability compared to maltodextrin.

Figure 3:
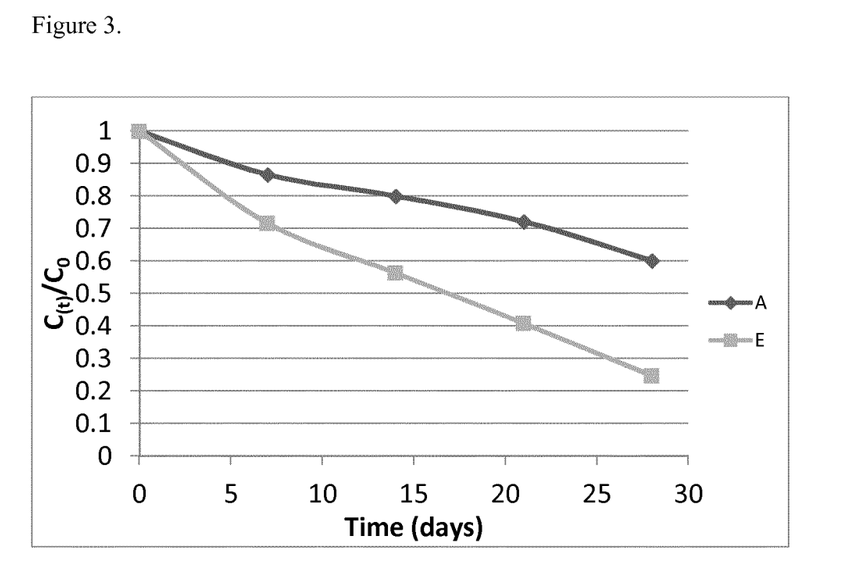
FIG. 3 shows vitamin A degradation curves at 60° C. and 68% RH for bran (rice) containing 20 wt. % of palm oil which contains 0.825 wt. % vitamin A palmitate (A), bran (rice) treated with 20 wt. % of hexane containing 0.825 wt. % vitamin A palmitate (E) (the hexane was then removed by evaporation).

FIG. 3 shows vitamin A degradation curves of either a mixture of vitamin A palmitate, palm oil and bran or vitamin A palmitate, hexane and bran. In the second mixture, hexane is used to homogeneously solubilize vitamin A and is then removed by evaporation. This procedure enables to address the vitamin A stabilizing effect of bran in the absence of oil. It can be seen that oil together with bran show the best ability to stabilize vitamin A, but bran alone is also able to stabilize vitamin A in the absence of oil.

The Oxygen Radical Absorbance Capacity (ORAC) value of bran alone and the two mixtures in FIG. 3 (all the same batch of rice bran) were measured. The ORAC assay relies on free radical damage to a fluorescent probe caused by an oxidizing reagent resulting in a loss of fluorescent intensity over time. Inhibition of oxidative damage to the fluorescent probe can be correlated with the antioxidant capacity of a compound acting as a free radical scavenger. ORAC results are given as Trolox® (an antioxidant) equivalents (TE), calculated from comparison to a Trolox® calibration curve.

| Sample | H-ORAC (µmol TE/100 g) |
|---|---|
| Rice bran | 8000 |
| Rice bran + Vitamin A (applied with hexane) | 8200 |
| Rice bran + Vitamin A + Palm Oil | 5700 |

The values for rice bran and rice bran with vitamin A are essentially the same, but when the vitamin A is dissolved in palm oil and added to the bran the ORAC value is significantly lower. This indicates that the antioxidant capacity has been reduced by the presence of the lipid. It is therefore surprising that the degradation curves of FIG. 3 show that bran together with lipid has the best ability to stabilize vitamin A. This suggests that the stabilization of the vitamin A by bran and lipid is not primarily an antioxidant effect. The exact cause of this surprising stabilization is not elucidated by this experiment but, without wishing to be bound by theory, the inventors believe that the lipid and bran provide physical protection for the lipid-soluble vitamin.

Figure 4:
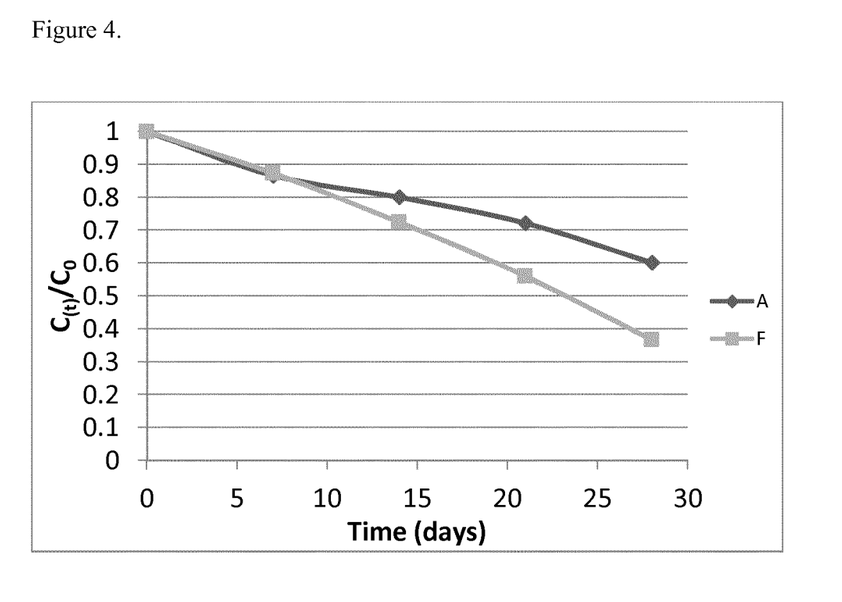
FIG. 4 shows vitamin A degradation curves at 60° C. and 68% RH for bran (rice) containing 20 wt. % of palm oil which contains 0.825 wt. % vitamin A palmitate (A) and bran (rice) containing 20 wt. % of palm oil which contains 0.825 wt. % vitamin A palmitate. This latter mixture was blended with 3.75% iron pyrophosphate powder (F).

In FIG. 4, a comparison of a mixture of vitamin A palmitate, palm oil and bran in the presence or absence of iron pyrophosphate is showed. Iron is known as a strong pro-oxidant that can be present in foods, either as a fortificant or naturally. Iron was reported to increase vitamin A degradation in food products. Here we show that the presence of iron indeed destabilizes the vitamin A, but the oil and bran keep a strong ability to stabilize vitamin A in this system.

Figure 5:
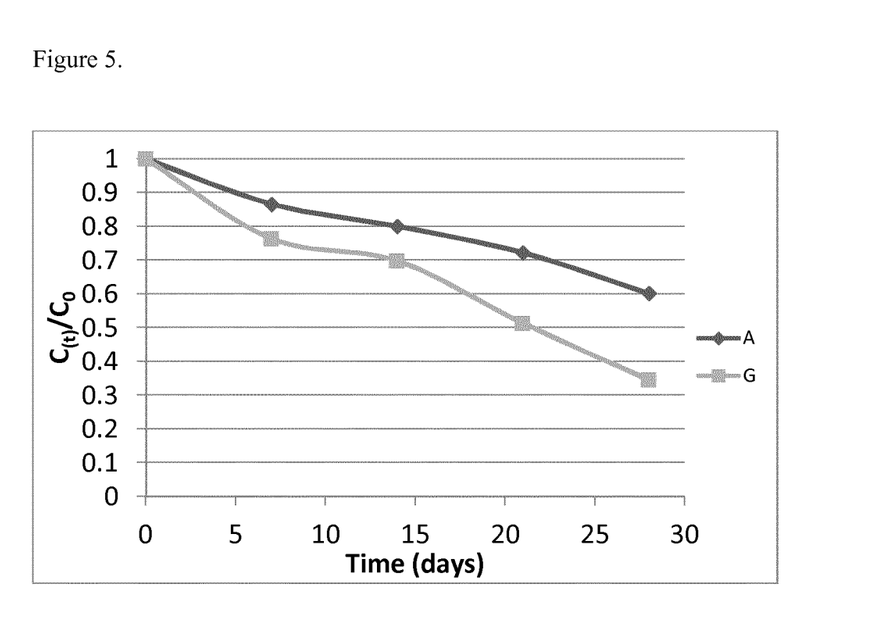
FIG. 5 shows vitamin A degradation curves at 60° C. and 68% RH for rice bran containing 20 wt. % of palm oil which contains 0.825 wt. % vitamin A palmitate (A) and wheat bran containing 20 wt. % of palm oil which contains 0.825 wt. % vitamin A palmitate (G).

FIG. 5 displays degradation curves of vitamin A when mixed with palm oil and different brans. This shows that at least rice and wheat brans are able to stabilize vitamin A palmitate in oil.

Figure 6:
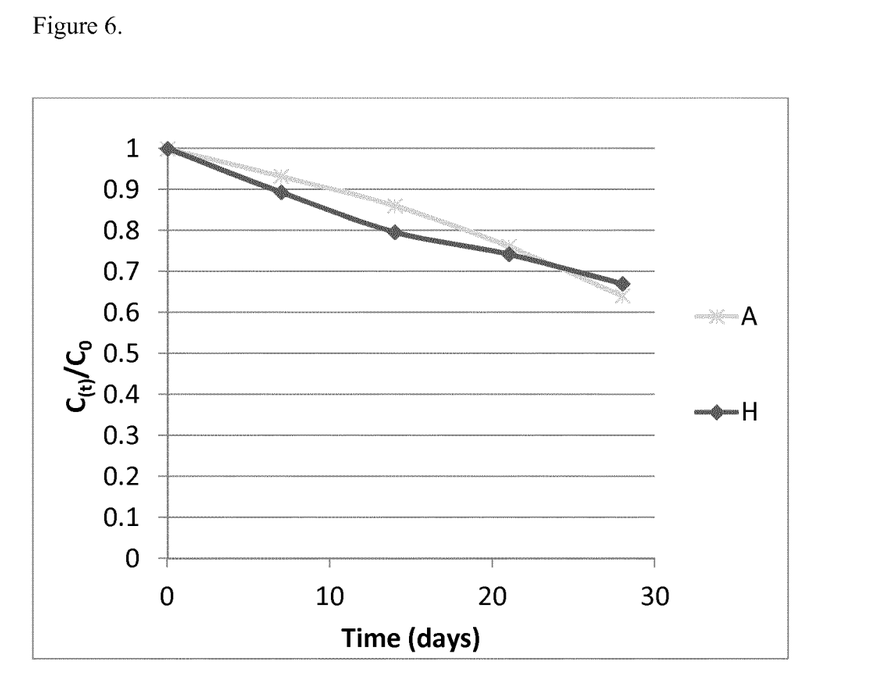
FIG. 6 shows vitamin A degradation curves at 60° C. and 68% RH for rice bran containing 20 wt. % of palm oil which contains 0.825 wt. % vitamin A palmitate (A) and rice bran phytic acid extracted containing 20 wt. % of palm oil which contains 0.825 wt. % vitamin A palmitate (H).

FIG. 6 shows the degradation of vitamin A mixed with palm oil and bran, comparing bran which has had phytic acid removed with bran where no phytic acid removal has taken place. The process of phytic acid removal would remove any water-soluble antioxidants which might be present in the bran, but the results show no difference between the brans. This indicates that the enhanced vitamin A stability observed with compositions comprising bran is not as a result of water-soluble antioxidants being present in the bran.

Example 2—Comparison of Bran-Stabilised Vitamin A with a Commercial Encapsulated Vitamin A Preparation Vitamin A preparations comprising vitamin A palmitate, oil and bran, or vitamin A palmitate, oil and maltodextrin, were prepared as described in Example 1. A commercial encapsulated vitamin A preparation in powder form, recognised as having excellent stability, was also obtained from DSM (Dry Vitamin A Palmitate 250 S/N-B).

Figure 7:
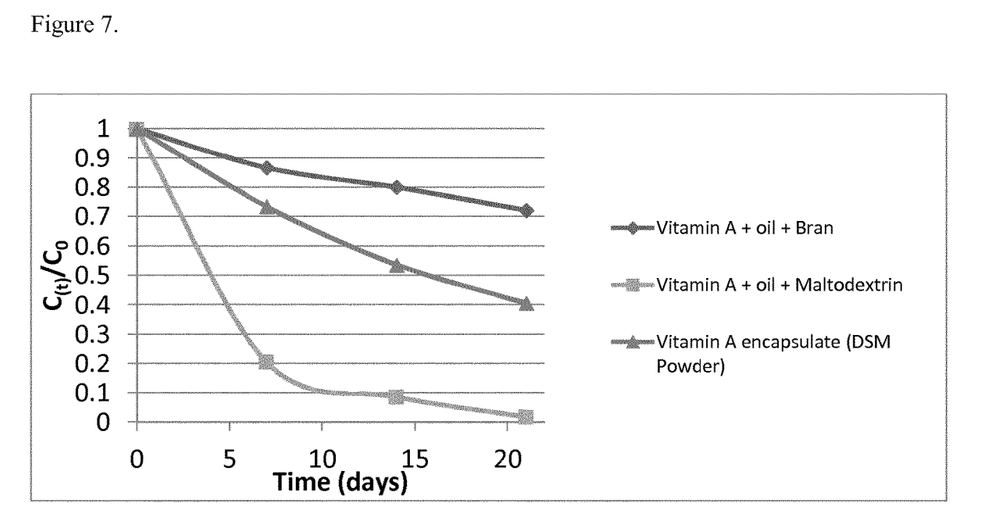
FIG. 7 shows vitamin A degradation curves at 60° C. and 68% RH for bran (rice) containing 20 wt. % of palm oil which contains 0.825 wt. % vitamin A palmitate (♦), maltodextrin containing 20 wt. % of palm oil which contains 0.825 wt. % vitamin A palmitate (■), or powdered vitamin A encapsulate from DSM (▲).

The three vitamin A preparations were tested for stability in the manner described in Example 1. The least stable preparation comprised vitamin A, oil and maltodextrin. The commercial preparation was significantly more stable than the maltodextrin preparation. However, the preparation comprising vitamin A, oil and bran according to the present invention had a greater stability than both of the other two preparations, this is despite the commercial encapsulated Vitamin A preparation containing 3% BHT antioxidant by weight. The level of antioxidants in this commercial encapsulated preparation is much higher than any naturally occurring antioxidants in the bran (typically below 0.3% of phenolic compounds, which would also be less efficient as antioxidants than BHT) so it is surprising that the preparation comprising vitamin A, oil and bran according to the present invention had such good stability. The results are shown in FIG. 7.

Example 3—Degradation During Heating of Bran Containing Oil and Vitamin A

Palm oil and vitamin A palmitate were liquefied at 70° C. and 50° C. respectively in water baths. The time of immersion of vitamin A palmitate was kept as brief as possible to allow the sample to melt but not degrade. MiliQ water (250 ml per sample) was heated up at 85° C. in an oven. In a 100-mL crystallizing dish, 0.0432 g of vitamin A palmitate and 5.38 g of palm oil were weighed and stirred for five minutes at 250 rpm in a 50° C. water bath. Subsequently, 21.3 g or bran (rice or wheat) were added and thoroughly mixed with the oil in a mortar to insure homogeneity of vitamin A in bran. When applicable, only the oil+vitamin A mixture was used for one set of samples.

Figure 8:
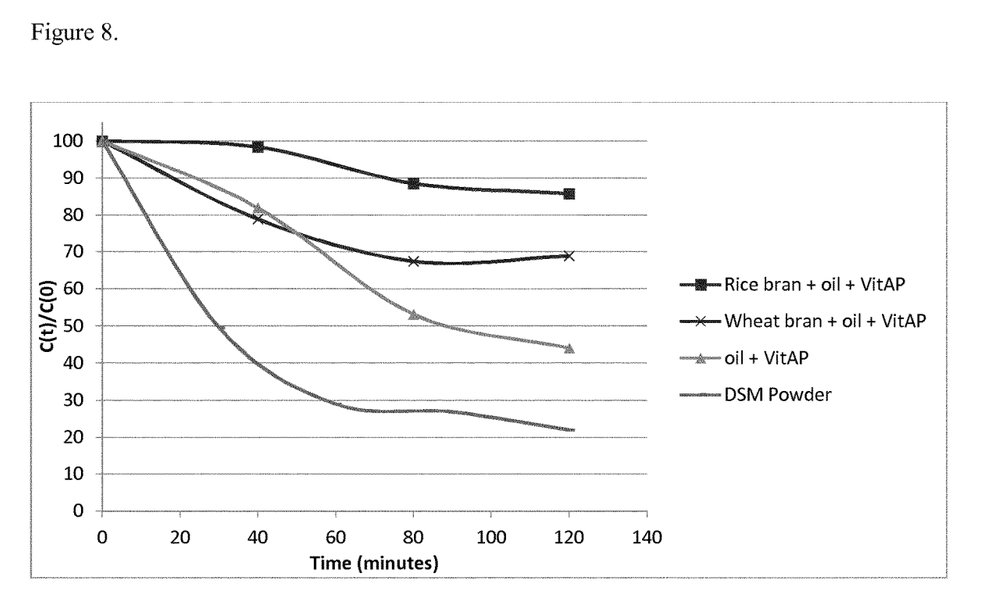
FIG. 8 shows vitamin A degradation curves at 98° C. in excess water for different brans containing 20% of palm oil which contains 0.825% of vitamin A palmitate (rice bran ■, wheat bran x), palm oil containing 0.825% of vitamin A (▲), and powdered vitamin A encapsulate from DSM (line with no marker).

The mixtures were dispersed using a Polytron® PT 3100 (Kinematica AG). The Polytron was pre-heated in a 400 ml beaker containing hot water (to avoid the oily phase of the emulsion sticking to the equipment). The bottom of another 400 ml beaker was dug into a 50° C. water bath for 30 seconds. The beaker was subsequently dried and placed on a balance. Then, 0.266 g of master mix prepared above was weighed in the hot beaker. In the case of the encapsulated vitamin A powder, 3 mg of this compound was weighed in a 400 ml beaker. For the vitamin A+oil mixture, 0.054 g of the solution were weighed in a 400 ml beaker. In all cases, a volume of 250 ml of hot MiliQ water was added to the beaker. The resulting solutions were subjected to the Polytron for 5 minutes at 17,000 rpm. Four aliquots of 15 g of the above dispersions were weighed in Pyrex culture tubes. The four tubes were closed and three of them were placed into heating blocks preheated at 98° C. to simulate simmering during cooking. One aliquot was taken out of heating block each 40 minutes and cooled down for 2 minutes in water at room temperature. The remaining tube corresponds to $T_0$, not heated. A volume of 13.7 µl of Tween 20 was added to each tube to stabilize the emulsion until analysis. All tubes were vortexed for 10 seconds and then incubated at 4° C. in a fridge before proceeding with analysis. All experiments were repeated at least twice. All prepared samples contained 0.825% vitamin A palmitate in oil. The degradation of vitamin A in the samples is shown in FIG. 8. The combination of oil and bran was surprisingly found to be considerably more effective at stabilizing vitamin A under conditions of simmering.

Further aspects and embodiments of the invention are set out in the following numbered paragraphs:

1. A composition comprising: (i) a mixture containing a lipid-soluble vitamin dissolved in a lipid, and (ii) bran; wherein the mixture is absorbed into and/or adsorbed onto the bran.

2. A composition according to paragraph 1, wherein the lipid-soluble vitamin is selected from the group consisting of: vitamin A, provitamin A, vitamin D, vitamin A ester, vitamin D ester, and combinations thereof.

3. A composition according to paragraph 1 or paragraph 2, wherein the lipid-soluble vitamin is selected from the group consisting of vitamin A, provitamin A and vitamin A ester, and combinations thereof.

4. A composition according to paragraph 2 or paragraph 3 wherein the ester is selected from an acetate or a fatty acid ester, and a combination thereof.

5. A composition according to any preceding paragraph wherein the lipid-soluble vitamin is selected from the group consisting of: vitamin A fatty acid ester and provitamin A, and a combination thereof.

6. A composition according to any preceding paragraph wherein the lipid-soluble vitamin is vitamin A fatty acid ester, preferably selected from the group consisting of retinyl palmitate, retinyl oleate, retinyl stearate and retinyl linoleate, and combinations thereof, preferably wherein the lipid-soluble vitamin is retinyl palmitate.

7. A composition according to any of paragraphs 1-5, wherein the provitamin A is beta-carotene or beta-cryptoxanthin.

8. A composition according to paragraph 1 or paragraph 2, wherein the lipid-soluble vitamin is selected from the group consisting of vitamin D and a vitamin D ester, and combinations thereof.

9. A composition according to paragraph 8 wherein the lipid-soluble vitamin is selected from the group consisting of: cholecalciferol (vitamin D3) and ergocalciferol (vitamin D2), an ester of cholecalciferol and an ester of ergocalciferol.

10. A composition according to paragraph 8 or paragraph 9, wherein the ester is selected from the group consisting of: acetate, palmitate, oleate, stearate and linoleate, preferably palmitate.

11. A composition according to any preceding paragraph, wherein the lipid is a fat (preferably wherein the fat is liquid at room temperature); preferably wherein the fat is a fish oil, animal fat (for example fat extracted from the rendered tissue of livestock animals such as pigs, chickens and cows, or dairy fats such as butter fat, or mixtures thereof) or vegetable fat (for example those selected from the group consisting of sunflower oil, rapeseed oil, cottonseed oil, coconut oil, cocoa butter, illipe fat, sal fat, shea fat, olive oil, palm oil, soybean oil, peanut oil, palm kernel oil, corn oil, grape seed oil, hazelnut oil, sesame oil and mixtures thereof), more preferably wherein the fat is selected from palm oil and sunflower oil or mixtures thereof; more preferably wherein the fat is palm oil.

12. A composition according to any preceding paragraph, wherein the bran is powdered bran, preferably wherein the powdered bran has a particle size of from: about 15 µm to about 1000 µm, for example about 50 µm to about 800 µm, about 75 µm to about 700 µm, about 100 µm to about 600 µm, or about 250 µm to about 500 µm.

13. A composition according to any preceding paragraph, wherein the bran is defatted bran, preferably wherein the defatted bran contains: less than about 5 wt. % fat, less than about 4 wt. % fat, less than about 3 wt. % fat, less than about 2 wt. % fat, less than about 1.5 wt. % fat, less than about 1 wt. % fat, or less than about 0.5 wt. % fat.

14. A composition according to any preceding paragraph wherein the bran has a reduced phytic acid content; preferably wherein the bran contains: less than about 5 wt. %, less than about 4 wt. %, less than about 3 wt. %, less than about 2 wt. %, less than about 1 wt. %, less than about 0.5 wt. %, or less than about 0.25 wt. % phytic acid.

15. A composition according to any preceding paragraph, wherein the bran is selected from rice bran, wheat bran, oat bran, and combinations thereof; preferably wherein the bran is rice bran.

16. A composition according to any preceding paragraph, wherein the weight ratio of (i) to (ii) is from: about 1:200 to about 1:1, about 1:100 to about 1:1.5, about 1:50 to about 1:2, about 1:20 to about 1:2, about 1:10 to about 1:2, or about 1:6 to about 1:3.

17. A composition according to any preceding paragraph, wherein the amount of lipid-soluble vitamin in the lipid is from about 0.1 wt. % to about 5 wt. %; preferably from about 0.1 wt. % to about 4 wt. %, about 0.1 wt. % to about 3 wt. %, about 0.1 wt. % to about 2 wt. %, or about 0.1 wt. % to about 1 wt. %.

18. A composition according to any preceding paragraph, wherein the bran comprises about 0.001 wt. % to about 1 wt. % lipid-soluble vitamin; preferably about 0.05 wt. % to about 1 wt. %, about 0.01 wt. % to about 0.5, about 0.05 wt. % to about 0.5 wt. %, about 0.1 wt. % to about 0.25 wt. %, or about 0.1 to about 0.2 wt. % lipid-soluble vitamin.

19. A composition according to any preceding paragraph, wherein the composition further comprises an antioxidant; preferably wherein the antioxidant is present in component (i), and more preferably wherein antioxidant is present at a concentration of: about 0.005 wt. % to about 0.5 wt. %, about 0.01 wt. % to about 0.5 wt. %, about 0.01 wt. % to about 0.4 wt. %, about 0.01 wt. % to about 0.2 wt. %, about 0.02 wt. % to about 0.4 wt. %, or about 0.02 wt. % to about 0.2 wt. % relative to the lipid in component (i), particularly wherein the antioxidant is present at a concentration of about: 0.005, 0.01, 0.02, 0.03, 0.04, 0.05, 0.1, 0.2, 0.3, 0.4, or 0.5 wt. % relative to the lipid in component (i).

20. A composition according to any preceding paragraph, wherein the composition further comprises an emulsifier;

preferably wherein the emulsifier is present in component (i); preferably wherein the emulsifier is lecithin, preferably wherein the emulsifier (preferably lecithin) is present at a concentration of: about 0.1 wt. % to about 30 wt, about 0.5 wt. % to about 30 wt. %, about 0.5 wt. % to about 20 wt. %, about 1 wt. % to about 20 wt. %, about 1 wt. % to about 10 wt. %, or about 2 wt. % to about 5 wt. % relative to the lipid in component (i), and more preferably, wherein the emulsifier is present at a concentration of about: 0.1, 0.5, 1, 2, 5, 10, or 30 wt. % relative to the lipid in component (i).

21. A composition according to any preceding paragraph, wherein the ratio of the amount of lipid-soluble vitamin present in the composition following a storage period of about 20 days at about 60° C. and about 68% relative humidity to the amount of lipid-soluble vitamin present in the composition at the start of the same storage period is at least 0.5:1; preferably at least 0.6:1, more preferably at least 0.7:1.

22. A composition according to any preceding paragraph, wherein the ratio of the amount of lipid-soluble vitamin present in the composition following exposure for about one hour to a temperature of about 98° C. to the amount of lipid-soluble vitamin present in the composition before said exposure is at least 0.8:1, preferably at least 0.9:1.

23. A composition according to any preceding paragraph which further comprises water, preferably wherein the water activity is: greater than about 0.3, greater than about 0.4, greater than about 0.45, greater than about 0.50, and more preferably wherein the composition has a water activity between about 0.3 and about 0.99, or between about 0.4 and about 0.95.

24. A process for preparing a composition according to any preceding paragraph, the process comprising the steps of:
   (a) dissolving a lipid-soluble vitamin in a lipid to form a mixture; and
   (b) combining the mixture with bran, for example wherein the lipid does not originate from the bran.

25 A process according to paragraph 24, wherein in step (b), the mixture is absorbed into and/or adsorbed onto the bran.

26. A process for providing a stabilised vitamin composition, the process comprising the steps of:
   (a) dissolving a lipid-soluble vitamin in a lipid to form a mixture; and
   (b) combining the mixture with bran, absorbing the mixture into and/or adsorbing the mixture onto the bran to provide a stabilized vitamin composition.

27. A process according to any of paragraphs 24-26, wherein the lipid-soluble vitamin is as defined in any of paragraphs 2-10.

28. A process according to any of paragraphs 24-27, wherein the lipid as defined in paragraph 11.

29. A process according to any of paragraphs 24-28 wherein the bran is as defined in any of paragraphs 12-15.

30. A process according to any of paragraphs 24-29, wherein the weight ratio of lipid to bran is from: about 1:200 to about 1:1, about 1:100 to about 1:1.5, about 1:50 to about 1:2, about 1:20 to about 1:2, about 1:10 to about 1:2, or about 1:6 to about 1:3.

31. A process according to any of paragraphs 24-30, wherein the amount of lipid-soluble vitamin in the lipid is from about 0.1 to about 5 wt. %; preferably from about 0.1 wt. % to about 4 wt. %, about 0.1 wt. % to about 3 wt. %, about 0.1 wt. % to about 2 wt. %, or about 0.1 wt. % to about 1 wt. %.

32. A process according to any of paragraphs 24-31, wherein the bran comprises about 0.001 wt. % to about 1 wt. % lipid-soluble vitamin; preferably about 0.05 wt. % to about 1 wt. %, about 0.01 wt. % to about 0.5, about 0.05 wt. % to about 0.5 wt. %, about 0.1 wt. % to about 0.25 wt. %, or about 0.1 to about 0.2 wt. % lipid-soluble vitamin.

33. A process according to any of paragraphs 24-32, wherein the weight ratio of the mixture containing lipid-soluble vitamin and lipid to bran is from: about 1:200 to about 1:1, about 1:100 to about 1:1.5, about 1:50 to about 1:2, about 1:20 to about 1:2, about 1:10 to about 1:2, or about 1:6 to about 1:3.

34. A composition obtainable by a process according to any of paragraphs 24-33.

35. A food product comprising a composition as defined in any of paragraphs 1-23 or 34.

36. A food product according to paragraph 35, wherein the food product is selected from the group consisting of: a dairy product, a culinary product, a food ingredient, a baked good, a beverage product, a beverage powder, a confectionary product, a pasta or noodle product, a milk powder, a soup, a sauce, a taste maker and a pet food.

37. A nutritional supplement comprising the composition as defined in any of paragraphs 1-23 or 34.

38. A nutritional supplement according to paragraph 37, wherein the nutritional supplement is a maternal supplement.

39. Use of bran for stabilising a lipid-soluble vitamin, wherein the lipid-soluble vitamin is dissolved in a lipid and wherein the lipid is absorbed into and/or adsorbed onto the bran, for example wherein the lipid does not originate from the bran.

40. Use according to paragraph 39, wherein the lipid-soluble vitamin is as defined in any of paragraphs 2-10.

41. Use according to paragraph 39 or paragraph 40, wherein the lipid as defined in paragraph 11.

42. Use according to any of paragraphs 39-41, wherein the bran is as defined in any of paragraphs 12-15.

The invention claimed is:

1. A food product consisting of a vitamin composition, the vitamin composition consisting of:
   a mixture containing a lipid-soluble vitamin dissolved in a vegetable oil;
   bran selected from the group consisting of defatted bran having less than about 5 wt. % fat, reduced phytic acid bran having less than about 5 wt. % phytic acid, and combinations thereof;
   optionally an antioxidant; and
   optionally an emulsifier; and
   optionally one or more minerals; and
   optionally water, and
   wherein the mixture is absorbed into and/or adsorbed onto the bran; the lipid-soluble vitamin is selected from the group consisting of vitamin A, provitamin A, vitamin A ester, and combinations thereof; and the vegetable oil is selected from the group consisting of palm oil and sunflower oil.

2. The food product according to claim 1, wherein the bran is selected from the group consisting of rice bran, wheat bran, oat bran, and combinations thereof.

3. The food product according to claim 1, wherein the weight ratio of the mixture to bran is from about 1:200 to about 1:1.

4. The food product according to claim 1, wherein the amount of the lipid-soluble vitamin in the vegetable oil is from about 0.1 wt. % to about 5 wt. %.

5. The food product according to claim 1, wherein a ratio of the amount of the lipid-soluble vitamin present in the food product following a storage period of about 20 days at about 60° C. and about 68% relative humidity to the amount of the lipid-soluble vitamin present in the food product or nutritional supplement at the start of the same storage period is at least 0.5:1.

6. A process for preparing a vitamin composition according to claim 1 comprising the steps of:
(a) dissolving a lipid-soluble vitamin in a lipid to form a mixture; and
(b) combining the mixture with bran.

7. A method for stabilizing a lipid-soluble vitamin composition onto bran according to claim 1 comprising the steps of:
(a) dissolving a lipid-soluble vitamin in a lipid to form a mixture; and
(b) combining the mixture with bran.

8. The food product according to claim 1, wherein the bran comprises rice bran.

9. The food product according to claim 8, wherein the rice bran is defatted rice bran having less than about 5 wt. % fat.

10. The food product according to claim 1, wherein the bran has less than about 5 wt. % phytic acid.

11. The food product according to claim 1, wherein the vegetable oil is palm oil.

12. The food product or nutritional supplement according to claim 1, wherein the provitamin A is beta-carotene or beta-cryptoxanthin.

13. The food product according to claim 1, wherein the vitamin A ester is vitamin A acetate or a vitamin A fatty acid ester (retinyl ester).

14. The food product according to claim 1, wherein the vitamin A ester is vitamin A palmitate (retinyl palmitate).

15. The food product according to claim 1, wherein the bran is powdered bran having a particle size from about 15 μm to about 1000 μm.

16. The food product according to claim 1, wherein the bran has less than about 0.5 wt. % phytic acid.

17. The food product according to claim 1, wherein the bran has less than about 0.25 wt. % phytic acid.

18. The food product according to claim 1, wherein the bran has less than about 0.5 wt. % fat.

* * * * *